US006448409B1

(12) United States Patent
Silks, III

(10) Patent No.: US 6,448,409 B1
(45) Date of Patent: *Sep. 10, 2002

(54) METHOD FOR THE SYNTHESIS OF CHIRAL ALLYLIC ALCOHOLS UTILIZING SELONE BASED CHIRAL DERIVATIZING AGENTS

(75) Inventor: Louis A. Silks, III, White Rock, NM (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/439,481

(22) Filed: Nov. 12, 1999

(51) Int. Cl.$^7$ .............................................. C07D 263/20
(52) U.S. Cl. ....................................... 548/229; 568/433
(58) Field of Search ........................... 548/229; 568/433

(56) References Cited

U.S. PATENT DOCUMENTS

| 5,068,345 A | * 11/1991 | Illig ............................ 548/239 |
| 5,344,936 A | * 9/1994 | Silks ........................... 548/229 |
| 5,801,249 A | * 9/1998 | Davies ......................... 548/229 |

FOREIGN PATENT DOCUMENTS

| JP | 6-340642 | * 6/1994 | .................. 548/229 |

OTHER PUBLICATIONS

Wu, Trends in Organic Chemistry, 7 105–114, 1998.*

* cited by examiner

Primary Examiner—Robert Gerstl
(74) Attorney, Agent, or Firm—James M. Ritchey

(57) ABSTRACT

Molecules containing a chiral 1,2-diol unit are synthesized from reactions between aldehydes and N-acyl selones. A chilled N-acyl selone is reacted with a Lewis acid such as TiCl$_4$ and mixed with a tertiary amine such as diisopropylethylamine to generate an enolate solution. Upon further chilling of the enolate solution a desired aldehyde is added and after an acceptable reaction period a quencher is introduced and the product isolated.

29 Claims, No Drawings

METHOD FOR THE SYNTHESIS OF CHIRAL ALLYLIC ALCOHOLS UTILIZING SELONE BASED CHIRAL DERIVATIZING AGENTS

This invention was made with Government support under Contract No. W-7405-ENG-36, awarded by the Department of Energy. The Government has certain rights in this invention

BACKGROUND OF THE INVENTION

1. Field of the Invention

A method for synthesizing chiral allylic alcohols is disclosed. More specifically, paired chiral diols that are anti (on opposite sides) or syn (on the same side) were generated by aldol reactions between selones (aldol acceptor) and various aldehydes (aldol donor).

2. Description of the Background Art

Aldol reactions have played a central role in many stereoselective constructions of carbon-carbon bonds. Evans reported in 1981 that a boron based enolate of an N-acylated 2-oxazolidinone underwent stereoselective carbon-carbon bond formation with aldehydes to give a syn aldol product.[1]

SUMMARY OF THE INVENTION

An object of the present invention is to provide a method of synthesizing 1,2-diol units.

Another object of the present invention is to disclose a method for producing an optically active or chiral 1,2-diol unit within a molecule.

A further object of the present invention is to relate a process for making chiral 1,2-diol containing molecules via an aldol reaction between a selone (aldol acceptor) and an aldehydes (aldol donor).

Still another object of the present invention is to describe a chiral 1,2-diol synthesis scheme that utilizes an aldol donor, an aldol acceptor, a Lewis acid, and a suitable amine under acceptable conditions.

Yet a further object of the present invention is to present synthesis scheme for making a chiral 1,2-diol that employs an aldehyde, an N-acyl selone prereacted with $TiCl_4$, and diisopropylethylamine under reaction producing conditions.

Generally, disclosed is a synthesis method for making chiral 1,2-diols from reactions between an aldehyde and an N-acyl selone. Chilled N-acyl selone is reacted with a Lewis acid and mixed with a suitable amine to generate an enolate solution. The temperature range for this reaction is from about room temperature to about –50° C., but may be higher or lower depending upon the reactants, but preferably between about room temperature and about –30° C. and more usually about 0° C. to about –15° C. Upon further chilling of the enolate solution a desired aldehyde is added and after an acceptable reaction period a quencher is introduced and the product isolated. The further chilling is to a temperature range of about room temperature to about –100° C. and usually about room temperature to about –90° C., although colder temperatures may be required depending upon the reactants, more usually about room temperature to about –80° C. (this temperature may in some cases vary during the time of the reaction).

More specifically, disclosed is a method comprising the steps of: obtaining an aldol donor or aldehyde; obtaining an aldol acceptor or N-acyl selone; generating the Lewis acid enolate of the N-acyl selone by adding the selected Lewis acid to the chilled solution of the N-acyl selone with the subsequent addition of a suitable amine, preferably a tertiary amine; cooling the combined mixture further and adding the aldehyde; allowing the combination to react until complete; quenching the reacted combination; and isolate the product.

Other objects, advantages, and novel features of the present invention will become apparent from the detailed description that follows, when considered in conjunction with the associated drawings.

DESCRIPTION OF THE PREFERRED EMBODIMENT

Referring now to the following written disclosure and the included schemes, table, and chemical formulas, there is shown a preferred embodiment of the subject synthesis method for producing chiral diols.

Optically active 1,2-diol units are widely distributed in natural products such as macrolides, polyethers, polyketides, and carbohydrates. Synthesis schemes for producing 1,2-diol containing compounds would be extremely useful techniques. Working with the landmark work of Evans[1], intensive efforts have given rise to a large number of chiral auxiliaries[2], achiral and chiral-based Lewis acids[3] and catalytic processes[4] for aldol reactions. The selenocarbonyl group has been exploited both as a chiral interrogation tool and as a platform for the development of new chemistries associated with selone based chiral derivatizing agents (CDA's).[5] A new type of aldol reaction has been discovered using chiral selone reagents (known as "chiral 2-oxazolidineselone reagents" which have the selenocarbonyl group) in which the selenocarbonyl plays a pivotal role in determining the stereoselectivity of these reactions. The synthesis method employing titanium-(IV) enolates of N-acyloxazolidin-2-selones reacting with a variety of aldehydes is disclosed herein.

For starting materials, quantities of N-acylated selones needed to be constructed. Based on previous NMR results using the [2-$^{13}$C] labeled valine derived selone in the study of the acylation reaction[6], a one-pot process was devised for the conversion of the oxazoline to the N-acylated selone. Treatment of the 4(S)-methyl-5(R)-phenyl-oxazoline 1 with lithium bis-(trimethylsilyl)amide gave rise to selective deprotonation at C2. Addition of elemental selenium, followed by slow warming to 0° C., allows for the selenium insertion into the C2 carbon lithium bond. As soon as the reaction is shown to be complete by TLC, the anion is quenched with the appropriate acid chloride. Use of propionyl chloride in this one-pot process has afforded a 95% yield of the N-acyl selone 2 (Scheme 1).

Scheme 1

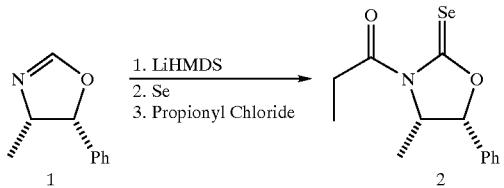

For example and not by way of strict limitation, the subject process usually begins by obtaining an aldol donor (aldehyde) and aldol acceptor (usually an N-acyl selone). Frequently, $TiCl_4$ utilized as the Lewis acid in generating a $TiCl_4$ enolate of the N-acyl selone. One method is by adding a methylene chloride solution of $TiCl_4$ to a 0° C. (a first reaction temperature) methylene chloride solution of the N-acyl selone and reacted for about five minutes (a first reaction period). After the five minutes, a tertiary amine such as Hunig's base, diisopropylethylamine, is added and stirred for about 30 minutes to about one hour and the same temperature (a second reaction period and second reaction temperature, respectively, with the first and second reaction temperatures the same in this example). The enolate solution is then chilled to a third reaction temperature of about −78° C. (this temperature be lower or may increase to room temperature depending on the donor and acceptor, see Table 1) and the obtained aldehyde added neat or as a solution in perhaps CH$_2$Cl$_2$ or the like. The mixture is stirred for a third reaction period (for detailed times see Table 1) until complete. The solution is then quenched (e.g. quenched with methanol until the solution becomes a yellow (for about a 1–10 mmol reaction about 1 mL of methanol is suitable). The solution is warmed to room temperature, if not there already, and filtered through a pad of silica gel. The silica gel is rinsed with about 30–40% (v/v) ethyl acetate/toluene solution, making sure the yellow product is removed from the white silica gel. The solvents are removed and the product purified by flash chromatography. As indicated above, this particular sequence or steps is only exemplary and not limiting for the subject process (see Table 1 and the Experimental Section of this disclosure for the exact details of various subject reactions).

It should be noted that the term "quenching" means to react the resulting product (aldol product or actually the titanium alkoxide if TiCl$_4$ is utilized) with a proton source such as ammonium chloride, methanol, or the like. This results is an isolatable product. Quenching the enolate can be done with an aldehyde or a proton source.

It was observed that the reaction of benzaldehyde with the titanium-based enolate of 2 gave one predominant product in good yield. Not only did the product appear to be stable and formed in good yield, but the reaction also gave the opposite syn isomer observed for an Evans-type process. Although rare, "unon-Evans" aldol reactions have been reported. The Crimmins[7] and Yan[8] groups recently reported some "non-Evans" aldols that employ thiocarbonyl-based CDA's. According to the reactions shown in Scheme 2, Table 1 illustrates the range of products that can be obtained using the subject selenium-based CDA's.

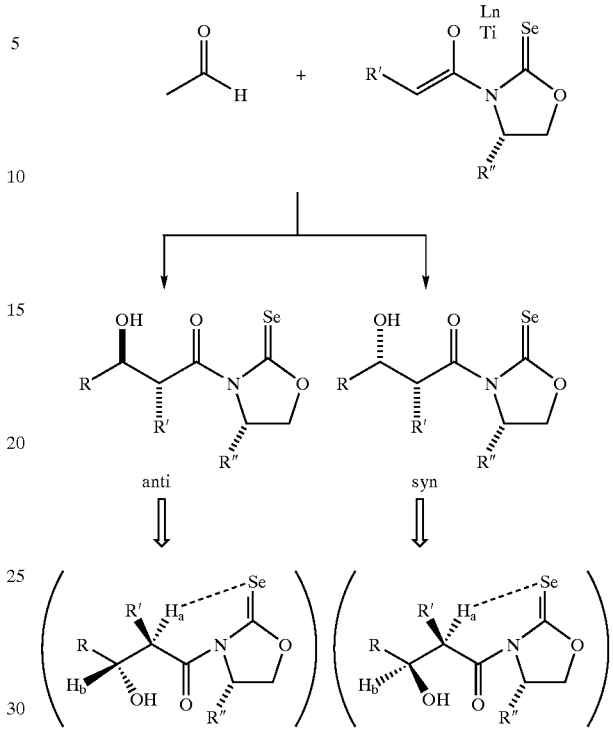

Scheme 2

TABLE 1

TiCl$_4$-Mediated Stereoselective Aldols

| Cmpd | R | R' | R″ | T (° C.) | t | yield (%) | yn:anti[a] | $\delta_H$[b] | J[c] | $\delta_{77_{Se}}$[d] | J[e] |
|---|---|---|---|---|---|---|---|---|---|---|---|
| 3 | Me$_2$CH | BnO | Me$_2$CH | −78 | 2.0 h | 72.0 | 5:12.5, 12.5 | 6.6[f] 6.9[h] 6.6[h] | 2.0[f] 8.7[h] 9.3[h] | 412.6[f] 423.6[h] 422.4[h] | 5.0[f] m[h] m[h] |
| 4 | Me$_2$CH | CH$_3$ | Bn | −78 | 15 m | 86.0 | >99:1 | 5.3 | 2.7 | 451.2 | 6.1 |
| 5 | Pr | BnO | Me$_2$CH | −78 | 2.0 h | 90.0 | 98:1, 1 | 6.5 | 2.1 | 428.5 | 4.7 |
| 6 | Pr | CH$_3$ | Bn | −78 | 15 m | 85.6 | >99:1 | 5.2 | 2.8 | 451.6 | 5.6 |
| 7 | MeCH=CH | BnO | Me$_2$CH | −78 | 2.0 h | 85.0 | 99:1 | 6.6 | 3.6 | 441.0 | 4.9 |
| 8 | MeCH=CH | CH$_3$ | Bn | −78 | 15 m | 85.6 | >99:1 | 5.3 | 4.2 | 444.3 | 5.3 |
| 9 | EtCH=CCH$_3$ | BnO | Me$_2$CH | −78 to Rt | 2.0 h | 63.0[k] | 61:39 | 6.8[f] 6.9[h] | 3.2[f] 7.2[h] | 419.0[f] 428.0[h] | 4.5[f] 4.2[h] |
| 10 | EtCH=CCH$_3$ | CH$_3$ | Bn | −78 | 15 m | 17.6 | >99:1 | 5.4 | 3.4 | 440.0 | 6.0 |
|  | EtCH=CCH$_3$ | CH$_3$ | Bn | −78 to −15 | 10 m | 87.0 | >99:1 | " | " | " | " |
| 11 | Ph | BnO | Me$_2$CH | −78 | 2.0 h | 97.0 | 99:1 | 6.9 | 3.2 | 432.8 | 4.3 |
| 12 | Ph | CH$_3$ | Bn | −78 | 15 m | 90.6 | >99:1 | 5.6 | 4.5 | 449.3 | 5.8 |
| 13 | BnOCH$_2$ | BnO | Me$_2$CH | −78 to −15 | 2.0 h | 91.0 | 43:26 | 6.6[f] | 2.4[f] | 431.9[f] | 4.7[f] |
|  | BnOCH$_2$[g] | BnO | Me$_2$CH | −78 to −15 | 2.0 h | 90.0 | <0.1:99.9 | 6.8 | 8.3 | 440.0 | 4.8, 1.5[i] |
| 14 | BnOCH$_2$ | CH$_3$ | Bn | −78 to −15 | 10 m | 91.8 | 50:50 | 5.3[f] | 4.3[f] | 447.2[f] | 5.5[f] |
|  | BnOCH$_2$[g] | CH$_3$ | Bn | −78 to −15 | 10 m | 99.4 | <0.1:99.9 | 5.5 | 7.0 | 441.1 | 5.5[j] |
| 15 | BuOCH$_2$[g] | CH$_3$ | Bn | −78 | 1.0 h | 81 | <0.1:99.9 | 5.4 | 7.9 | 439.1 | m |
| 16 | BuOCH$_2$[g] | BnO | Me$_2$CH | −78 | 1.0 h | 86 | 1:99 | 6.6 | 8.5 | 440.6 | .8, 1. |
| 17 | BnOCH(CH$_3$)[g,1] | CH$_3$ | Me$_2$CH | −78 | 1.0 h | 85 | <0.1:99.9 | 5.6 | 9.1 | 424.2 | m |
| 18 | BnOCH(CH$_3$)[g,1] | BnO | Me$_2$CH | −78 to −30 | 2.0 h | 95 | 1:97, 2 | 6.7 | 9.3 | 440.1 | m |

[a]Measured by $^3$H integration of Ha and/or by integration of the $^{77}$Se signals.
[b]$\delta_H$ of Ha in ppm5
[c]Ha (J$_{Ha-Hb}$).
[d]$\delta_{77_{Se}}$ of major isomer in ppm (relative to diphenyldiselenide at 465 ppm).
[e]J$_{1Ha-77Se}$.
[f]Data for syn isomer.
[g]The aldehyde was precomplexed with 1.05 equiv of TiCl$_4$ at −78° C.
[h]Data for anti isomer.

TABLE 1-continued

TiCl₄-Mediated Stereoselective Aldols

| Cmpd | R | R' | R" | T (° C.) | t | yield (%) | yn:anti[a] | $\delta_H$[b] | J[c] | $\delta_{77Se}$[d] | J[e] |
|------|---|----|----|----------|---|-----------|------------|---------------|------|--------------------|------|

[i]Four spin systems couple to the Se.
[j]Apparent d.
[k]Crude yield from NMR.
Aldol could not be purified.
[l]Derived from ethyl (S)-(−)-lactate.

The scope of the aldol process was evaluated using the propanoyl and glycolate selone adducts with α-aryl, -alkyl, -alkenyl, and -n-butyloxy and -benzyloxy atdehydes. The reaction of the N-propionyl selone enolates with uncomplexed aldehydes gives rise to the syn ("non-Evans") products in yields ranging from 85–92% and with good selectivity (>98%). For example, to a $CH_2Cl_2$ solution containing the N-acylated selone, the $TiCl_4$ (1.1 equiv) was added dropwise at −15° C. This mixture was stirred for 5 min, followed by the dropwise addition of Hunig's base (diisopropylethylamine) (1.15 equiv). The solution was stirred for an additional 30 min then cooled to −78° C., and 1.2 equiv of the aldehyde were added. The reaction mixture was stirred for the appropriate amount of time (Table 1). The reaction was quenched with 2 mL of methanol. Filtration through a pad of silica gel, followed by washing with a 40% ethyl acetate/toluene mixture (v/v), afforded a bright yellow solution. The ethyl acetate/toluene mixture effects the azeotropic removal of methanol. Carrying out the concentration step without toluene gives rise to a solution highly enriched with methanol, which causes decomposition of the selone adducts (red precipitate forms). Flash silica gel chromatography can be visually monitored because all of the aldol selone adducts prepared to date are bright yellow.

The use diisopropylethylamine or Hunig's base as a suitable amine is preferred, but other equivalent tertiary amines would be acceptable and within the scope of this disclosure.

For aldol 10 the more sterically demanding 2-methyl-2-propenal required higher temperatures for the reaction to proceed to completion. We were especially pleased to observe that the glycolate selone adducts enolized quite readily and presumably with chelation of the α-benzyloxy group, giving rise to the Z-enolate.[9] Addition of α-aryl, -alkyl, and -alkenyl aldehydes to this enolate solution gave rise to the "non-Evans" aldols (Table 1, compounds 5, 7, and 11). It is stressed that other heteroatoms instead of oxygen may be used and even "non-carbon" species (i.e. sulfur, selenium, and phosphorus) are possible including, but not limited to: α-amino aldehydes, α-sulfides, α-selenides, and the like (Note: the α-amino aldehydes would lead to amino containing carbohydrates that have numerous medical uses and the N-acyl selone could have a protected α-amino functionality that would undergo enolization and react with aldehydes). Lower yields and selectivities were observed for the glycolate enolates when 2-methylpropionaldehyde and 2-methyl-2-pentenal were used (Table 1, compounds 3, 9). Again, this was attributed to the increased steric demand of these aldehydes. Interestingly, the use of benzyloxyacetaldehyde with the glycolate selone has given rise to an anti selective aldol (Table 1, compounds 13, 14). If the benzyloxyacetaldehyde was not precomplexed with $TiCl_4$, the reaction gave little or no diastereoselectivity. However, precomplexation of the benzyloxyacetaldehyde with 1.05 equiv of $TiCl_4$ gave rise to excellent diastereoselectivity (>99% by ¹H and ⁷⁷Se NMR spectroscopy). The anti relationship between the two new chiral centers that are generated in this carbon-carbon bond forming reaction is supported by the proton-proton coupling constant (J=8.3 Hz).[10] Especially in aldol reactions, this type of anti relationship is one of the more difficult to access with high levels of diastereoselectivity.[11] In an effort to establish the generality of the anti selective aldol process, an additional four anti aldol products were constructed using this method (Table 1, compounds 15, 16, 17, and 18).

Usually $TiCl_4$ is utilized in the subject reaction, however, other Lewis acids may be used in equivalent reactions and are considered to be within the realm of this disclosure. Such Lewis acids would include, but not be limited to: $AlCl_3$, $BX_3$ (where X is a halide), $AlMeCl_2$, $AlMe_2Cl$, $ZnCl_2$, $MgCl_2$, $MgBr_2$ and the like.

The selone auxiliary can easily be removed using a variety of methods. We have reduced aldol amide 4 with $LiBH_4$ to give the corresponding 1,3 diol in 98% yield. The selone CDA was recovered in 95% yield. The optical rotation of the resulting diol indicated an ee which compares favorably with the ee of the parent chiral selone.[12] Hydrolysis to the β-hydroxy acid is effected within 5 minutes using LiOH. The end point is reached when the yellow aldol solution becomes nearly colorless. Direct conversion of the aldols to esters (81%) or the Weinreb amide was effected with DMAP using the mild Yan procedure[13]. Following this process and monitoring the reaction for completion by thin layer chromatography, conversion of the selone adducts to the ester or Weinreb amide is effected. Reduction of the adductions with 2.0 equiv of $LiBH_4$ in THF at 0° C. gave rise to the 1,3 diol.

Our structural investigations which were initially targeted to gain insight into the orientation and high selectivitives shown for these selone aldol reactions have led to the observation of C—H—Se through-space interactions in all of the aldol products. For selected derivatives, see below, single-crystal x-ray analysis indicated C—H—Se distances of 2.63, 2.71, and 2.72 Å, which are sub-Van der Waals.

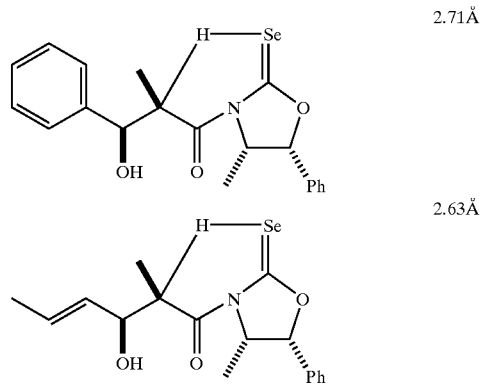

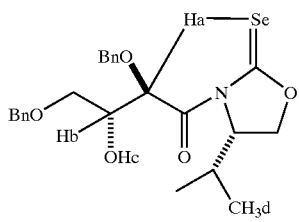

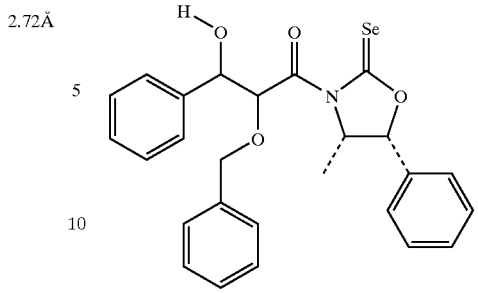

The $\delta_H$ of the aldol $H_a$ resonates between 5.2–6.9 ppm, which indicates that significant deshielding of this proton is occurring. To date, for all of the aldols we have investigated we have observed JSH couplings (Table 1, final column). For the syn aldols there is a unique doublet in each proton coupled ($H_a$) selenium spectrum, J=5–6 Hz, indicating the β-hydroxyl group is apparently not hydrogen bonding to the selenium as we initially expected. For the anti aldols the 1D proton coupled $^{77}$Se spectra exhibited more than one spin system interacting with the selenium. The gradient selected $^{1}$H/$^{77}$Se HMQC spectrum of anti-13 displayed interactions of 4 spin systems with the selenium. The major H—Se interactions arose from both the α-methine ($H_a$) and β-hydroxy hydrogen, while weak but clearly observable interactions resulted from the β-methine hydrogen and one of the methyl groups on the CDA isopropyl group. There are numerous reports of C—H—O interactions, and there is an increasing acceptance that these weak, unusual hydrogen bonds play significant roles as control elements in supramolecular complexes.[14] There are fewer reports of C—H—S interactions[15], and there are only two reports of C—H—Se interactions. Tomoda[16] and coworkers reported the shortest C—H—Se distance of 2.94 Å, while Vij and coworkers[17] have reported distances of 2.98 and 3.26 Å for their Sapphyrin molecules. A fundamental new type of non-opportunistic hydrogen bond has been uncovered in the investigated aldols.

Schemes 3 and 4 depict the generalized subject method for two different aldehydes (see the Experimental section below for reaction conditions for various aldehydes).

Scheme 3

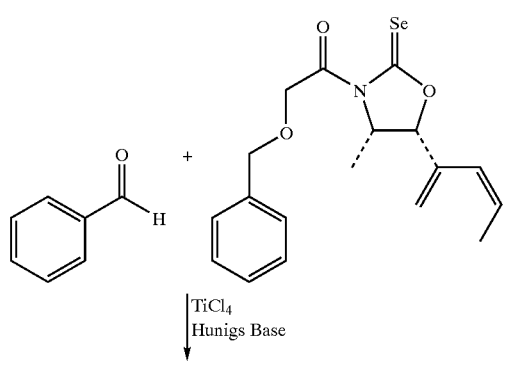

Scheme 4

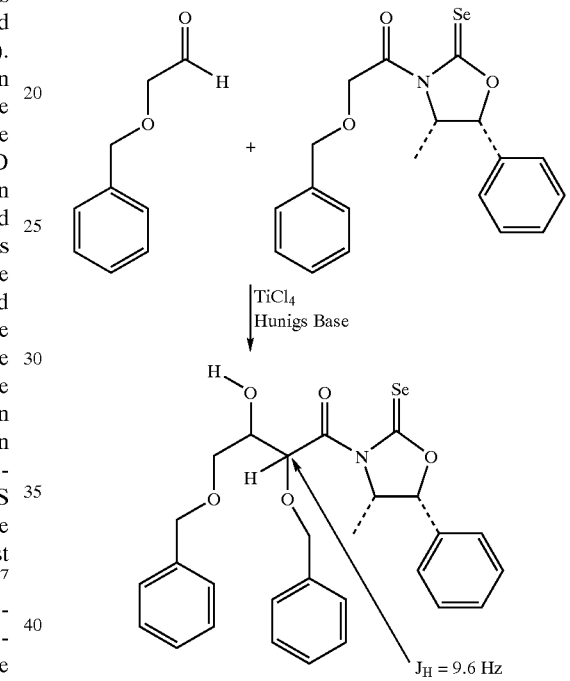

Scheme 5 presents the removal of the selone portion of a typical intermediate.

Scheme 5

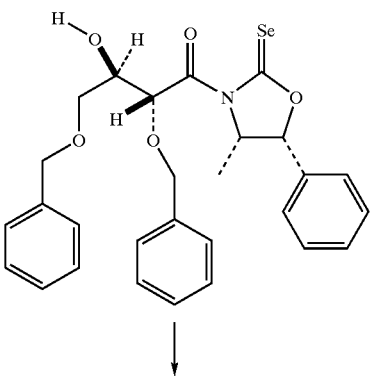

-continued

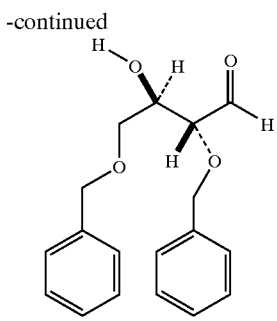

EXPERIMENTAL SECTION

General. IR spectra were recorded using KBr pellets. $^1$H, $^{13}$C and $^{77}$Se spectra were performed using CDCl$_3$ solutions (unless otherwise noted) at 300 MHz, 75.48 MHz and 57.26 MHz. $^1$H, $^{13}$C and $^{77}$Se chemical shifts are reported in ppm and referenced to TMS, CDCl$_3$, and diphenyl diselenide, respectively. All air-sensitive reaction were performed under an argon atmosphere using oven-dried glassware. Tetrahydrofuran (THF) and dichloromethane were freshly distilled from benzophenone ketyl and calcium hydride, respectively. Flash column chromatography was performed using EM Science silica gel 60 Å (230–400 mesh). Silica thin layer chromatography was done using EM Science plates (silica gel 60, F254, 0.15 mm).

Scheme 6

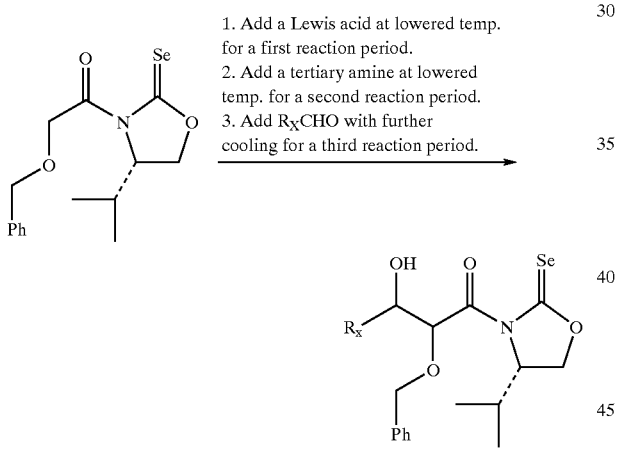

Where R$_X$CHO is:

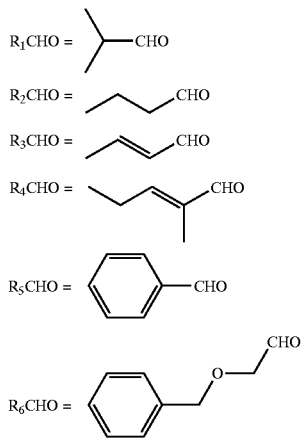

General procedure for the aldol reaction of (4S)-3-oxopropyl-4-phenylmethyl-2-oxazolidineselone with alde-hydes R$_1$ to R$_6$.(see Scheme 6 above for a presentation of the subject aldol reaction) TiCl$_4$ (1.0 M in CH$_2$Cl$_2$, 0.93 mL, 0.93 mmol, 1.2 equiv) was added in a solution of (4S)-3-oxopropyl- 4-phenylmethyl-2-oxazolidineselone at −17° C. (230 mg, 0.78 mmol) in CH$_2$Cl$_2$ (45 mL), The mixture was stirred for 15 min. N,N-Diisopropylethylamine (162 μL, 0.93 mmol, 1.2 equiv) was added. The mixture was stirred for 45 min and then cooled to −78° C. A solution of aldehyde (0.93 mmol) in CH$_2$Cl$_2$ was added slowly along the cooled glass wall. The mixture was stirred at −78° C. for 15 min. In the cases of aldehydes R$_1$, R$_2$, R$_3$ and R$_5$, methanol(0.5 mL) was added at −78° C. In the cases of aldehydes R$_4$ and R$_6$, the mixture was warmed to −15° C. and stirred for 10 min at −15° C., then methanol (0.5 mL) was added. The mixture was warmed to room temperature, then filtered through a short pack of silica gel. eluting with toluene/ethylacetate (70/30). After evaporation of the solvent, the residue was chromatographed on a column of silica gel, eluting with hexanes/ethylacetate (95/5) to give pure aldol. General procedure for the aldol reaction of (4S)-4-(1-methylethyl)-3-[(phenylmethoxy)acetyl]-2-oxazolidineselon and aldehydes R$_1$ to R$_6$ in the presence of TiCl$_4$ in CH$_2$Cl$_2$. TiCl$_4$ (1 M in CH$_2$Cl$_2$, 0.53 mL, 1.05 equiv) was added in a solution of (4S)-4-(1-methylethyl)-3-[(phenylmethoxy)acetyl]-2-oxazolidineselone (170 mg, 0.50 mmol) in CH$_2$Cl$_2$ (10 mL), at −17° C. The mixture was stirred for 15 min then N,N-Diisopropylethylamine (92 μL, 0.53 mmol, 1.05 equiv) was added. The mixture was stirred for 45 min and then cooled to −78° C. A solution of aldehyde (0.53 mmol ) in CH$_2$Cl$_2$ was added slowly onto the top portion of the inner glass wall. This ensures the aldehyde solution is chilled before entering into the reaction mixture. The mixture was stirred at −78° C. for 2 h. Methanol (0.5 mL) was added at −78° C. The mixture was warmed to room temperature, then filtered through a short pad of silica gel. The products were eluted with toluene/ethylacetate (70/30; v/v) solution. After evaporation of the solvent, the residue was immediately chromatographed on a column of silica gel, eluting with hexanes/ethylacetate (95/5; v/v) to give the pure aldol.

Reduction of (4S)-3-(2,4-dimethyl-3-hydroxyl-1-oxopentyl)-4-(phenylmethyl)-2-oxazolidineselone. Lithium borohydride (2.5 mL of a 2.0 M solution in THF, 5.0 mmol, 2.2 equiv) was added slowly to a cold (0°) solution of (4S)-3-(2,4-dimethyl-3-hydroxyl-1-oxopentyl)-4-(phenylmethyl)-2-oxazolidineselone (913.15 mg, 2.21 mmol) in THF (5 mL). The solution was stirred at 0° C. for 2 hrs. Then 2 mL of H$_2$O was added. The THF was evaporated under reduced pressure. The aqueous layer was extracted with ethylacetate (5 mL×4). The organic layer was dried over sodium sulfate and then filtered. The solvent was removed under reduced pressure. Purification of the residue by silica gel column chromatography (hexane/EtOAc; 9/1; v/v) afforded 263 mg (90%) of 2S, 3S-(+)-2,4-dimethyl-1, 3-pentanediol [α]$^{25}_D$=+10.4 (c=0.00582, CHCl$_3$); $^1$H NMR δ 3.77 (dd, 1H, J=11.7 Hz, J=4.7 Hz), 3.71 (dd, 1H, J=11.7 Hz, J=6.0 Hz), 3.42 (dd, 1H, J=10.0 Hz, J=2.7 Hz), 2.09 (br s, 1.7 H, OH), 1.85 (m, 1H), 1.7 (m, 1H), 1.60 (br s, 0.3H, OH), 1.01 (d, 3H, J=6.6 Hz), 0.97 (d, 3H, J=7.1 Hz), 0.88 (d, 3H, J=6.7 Hz); $^{13}$C NMR δ 80.02, 68.06, 36.16, 31.43, 19.31, 19.02, 8.92.

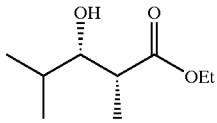

Ethyl (2S, 3S)-3-hydroxy-2,4-dimethyl-Pentanate. Absolute ethanol (2.0 mL) and 4-dimethylaminopyridine (82 mg, 0.67 mmol) was added to a solution of (4S)-3-(2,4-dimethyl-3-hydroxyl-1-oxopentyl)-4-(phenylmethyl)-2-oxazolidineselone (200 mg, 0.65 mmol) in $CH_2Cl_2$. The resulting solution was stirred at room temperature for 6 h. The solvent was removed under reduced pressure. Purification of the residue by silica gel column chromatography (hexane/Ether; 8/2; v/v) afforded 140 mg (81%) of ethyl (2S, 3S)-3-hydroxy-2,4-dimethyl-pentanate. $^1H$ NMR δ 4.20 (q, 2H, J=7.2 Hz), 3.59 (dd, 1H, J=8.0 Hz, J=3.7 Hz), 2.68 (dq, 1H, J=7.2 Hz, J=3.7 Hz), 2.5 (br s. 1H). 1.71 (h, 1H, J=6.7 Hz), 1.30 (t, 3H, J=7.2 Hz), 1.20 (d, 3H, J=7.2 Hz), 1.04 (d, 3H, J=6.7 Hz), 3H, J=6.7 Hz); $^{13}C$ NMR ($CDCl_3$, 75.48 MHz): 176.66, 76.75, 60.60, 41.72, 30.53, 19.02, 18.63, 14.12, 10.17

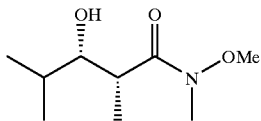

(2S,3S)-3-Hydroxy-N-mothoxy-N,2,4-trimethyl-pentanamide. N,O-Dimethylhydroxyl-amine hydrochloride (380 mg, 3.90 mmol) and 4-dimethylaminopyridine (244 mg, 2.00 mmol) was added to a solution of (4S)-3-(2,4-dimethyl-3-hydroxyl-1-oxopentyl)-4-(phenylmethyl)-2-oxazolidineselone (616 mg, 2.00 mmol) in $CH_2Cl_2$ (10 mL). The resulting solution was stirred at room temperature for 4 days. The solvent was removed under reduced pressure. Purification of the residue by silica gel column chromatography ($CH_2Cl_2$/ether; 95/5; v/v) afforded 210 mg (55%) of 3-hydroxy-N-methoxy-N,2,4-trimethyl-pentanamide. $^1H$ NMR δ 3.94 (br s, 1H), 3.72 (s, 3H), 3.45 (dd, 1H, J=8.4 Hz, J=2.1 Hz), 3.21 (s, 3H), 3.10 (br m, 1H), 1.73 (m, 1H), 1.16 (d, 3H, J=7.1 Hz), 1.04 (d, 3H, J=6.6 Hz), 0.88 (d, 3H, J=6.8 Hz); $^{13}C$ NMR δ 178.48, 76.90, 61.48, 35.72, 31.88, 30.20, 19.16, 18.90, 9.90

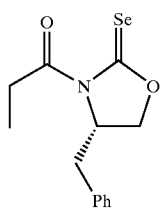

(4S)-3-oxopropyl-4-phenylmethyl-2-oxazolidineselone. $^1H$ NMR δ 7.33 (m, 5H), 5.00 (m, 1H), 4.42 (dd, 1H, J=9.4 Hz, J=2.5 Hz), 4.31 (ddd, 1H, J=7.7 Hz, J=9.4 Hz, J=0.8 Hz), 3.60 (qd, J=18.50 Hz, J=7.20 Hz), 3.43 (qd, J=18.5 Hz, J=7.20 Hz), 3.35 (dd, J=13.3 Hz, J=3.5 Hz), 2.81 (dd, 1H, J=14.3 Hz, J=10.1 Hz), 1.28(t, 3H, J=7.2 Hz); $^{13}C$ NMR δ 188.70, 174.97, 135.11, 129.40, 129.07, 127.47, 72.13, 65.59, 37.60, 32.27, 8.56 77; Se NMR δ 458.7 (br s).

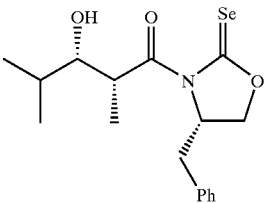

(4S)-3-(2,4-dimethyl-3-hydroxyl-1-oxopentyl)4-(phenylmethyl)-2-oxazolidineselone. Yield: 86.0%. IR (KBr, $cm^{-1}$) 3500, 2964.8, 1711.4, 1368.3, 1200.3, 1151.2, 948.2, 738.1, 696.1, 605.1, 500; $^1H$ NMR δ 7.40 (m, 5H), 5.32 (dq, 1H, J=7.0 Hz, J=2.7 Hz), 5.00 (m, 1H), 4.40 (dd, 1H, J=9.4 Hz, J=3.0 Hz), 4.30 (m, 1H), 3.76 (m, 1H), 3.36 (dd, 1H, J=13.3 Hz, J=3.5 Hz), 2.79 (m, 2H), 1.80 (m, 1H), 1.28 (d, 3H, J=8.8 Hz), 1.12 (d, 3H, J=6.6 Hz), 1.00 (d, 3H, J=6.8 Hz); $^{13}C$ NMR δ 188.58, 179.11, 135.02, 129.33, 129.09, 127.52, 76.51, 72.07, 60.80, 40.15, 37.70, 31.10, 19.44, 18.98, 10.26; $^{77}Se$ δ 451.2 (d, J=6.1 Hz); anti isomer $^{77}Se$ δ 459.0 Anal. Calcd for $C_{17}H_{23}NO_3Se$: (formula weight 368.34), C, 55.44; H, 6.29; N, 3.80. Found: C, 55.16; H, 6.44; N, 3.60. HRMS (FAB) m/z 370.0919 (370.0922 calcd for $C_{17}H_{24}NO_3Se$; M+H)

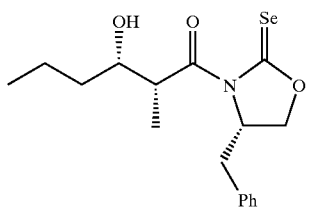

(4S)-3-(3-hydroxyl-2-methyl-1-oxohexyl)-4-(phenylmethyl)-2-oxazolidineselone. Yield: 85.6%. IR (KBr, $cm^{-1}$) 3600, 3024.5, 2963.8, 1707.4, 1457.5, 1380, 1194.5, 937.4, 748.3, 700.9, 505.1; $^1H$ NMR δ 7.40 (m, 5H), 5.16 (dq, 1H, J=7.0 Hz, J=2.8 Hz), 5.00 (m, 1H), 4.40 (dd, 1H, J=9.4 Hz, J=2.8 Hz), 4.30 (m, 1H), 4.17 (m, 1H), 3.35 (dd, 1H, J=13.3 Hz, J=3.6 Hz), 2.79 (dd, 1H, J=13.3 Hz, J=10.2 Hz), 1.50 (m, 4H), 1.28 (d, 3H, J=7.0 Hz), 1.02 (t, 3H, J=7.0 Hz) $^{13}C$ NMR δ 188.78, 178.21, 134.99, 129.36, 129.08, 127.52, 72.06, 71.41, 60.79, 42.10, 37.74, 35.88, 19.21, 14.06, 10.36; $^{77}Se$ δ 451.60 (d, J=5.6 Hz); ); anti isomer $^{77}Se$ δ 455.5. HRMS (FAB) m/z 370.0911 (370.0922 calcd for $C_{17}H_{24}NO_3Se$, M+H)

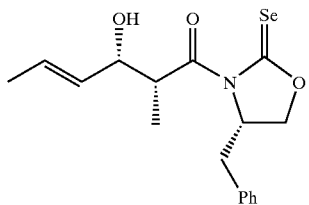

(4S)-3-(3-hydroxyl-2-methyl-1-oxo-4-hexen-1-yl)-4-(phenylmethyl)-2-oxazolidineselone. Yield: 85.6%. IR (KBr, $cm^{-1}$) 3600, 3020.8, 2971.8, 2936.8, 1760.6, 1704.4, 1494.3, 1452.3, 1361.3, 1193.2, 1109.2, 1052.3, 969.0, 950.0, 696.1, 612.1, 507; $^1H$ NMR δ 7.40 (m, 5H), 5.85 (dqd, 1H, J ×15.5, J=6.5, J=1.2 Hz), 5.65 (qdd, 1H, J=15.5 Hz, J=6.4 Hz, J=1.6 Hz), 5.30 (dq, 1H, J=6.9 Hz, J=4.2 Hz), 5.04 (m, 1H), 4.65 (m, 1H), 4.39 (dd, 1H, J=9.4 Hz, J=3.0 Hz), 4.31 (ddd, J=9.4 Hz, J=7.8 Hz, J=0.8 Hz), 3.32 (dd, 1H, J=13.4 Hz, J=3.6 Hz), 2.78 (dd, 1H, J=13.4 Hz, J=10.1 Hz), 2.72 (d, 1H, J=3.4 Hz), 1.79 (ddd, 3H, J=6.5, J=1.6 Hz), J=0.96 Hz), 1.28 (d, 3H, J=6.9 Hz); $^{13}$C NMR δ 188.93, 177.01, 134.99, 129.98, 129.36, 127.07, 128.60, 127.51, 73.40, 72.07, 60.77, 42.68, 37.72, 17.82, 11.61; $^{77}$Se NMR δ 444.29 (d, J=5.3 Hz); ); anti isomer $^{77}$Se δ 453.0. HRMS (FAB) m/z 368.0751 (368.0766 calcd for $C_{17}H_{22}NO_3Se$, M+H)

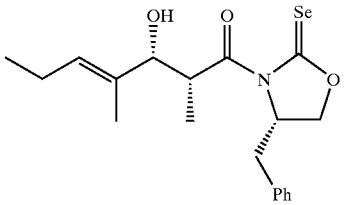

(4S)-3-(2,4-dimethyl-3-hydroxyl-1-oxo-4-hepten-1-yl)-4-(phenylmethyl)-2-oxazolidineselone. Yield: 87.0%. IR (KBr, cm$^{-1}$) 3600, 2964.8, 2929.8, 2866.8, 1781.4, 1718.4, 1452.3, 1375.3, 1214.3, 1151.2, 1109.2, 941.2, 703.1, 549.1; $^1$H NMR δ 7.40 (m, 5H), 5.16 (dq, 1H, J=7.0 Hz, J=2.8 Hz), 5.00 (m, 1H), 4.40 (dd, 1H, J=9.4 Hz, J=2.8 Hz), 4.30 (m, 1H), 4.17 (m, 1H), 3.25 (dd, 1H, J=13.3 Hz, J=3.6 Hz), 2.79 (dd, 1H, J=13.3 Hz, J=10.2 Hz), 1.50 (m, 4H), 1.28 (d, 3H, J=7.0 Hz), 1.02 (t, 3H, J=7.0 Hz); $^{13}$C NMR δ 188.78, 178.21, 134.99, 129.36, 129.08, 127.52, 72.06, 71.41, 60.79, 42.10, 37.74, 35.88, 19.21, 14.06, 10.36; $^{77}$Se δ (d, J=5.6 Hz). Anal. Calcd for $C_{19}H_{25}NO_3Se$ (formula weight=394.60), C, 57.88; H, 6.40; N, 3.55. Found: C, 58.04; H, 6.42; N, 3.48.

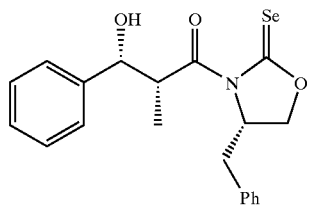

(4S)-3-3-hydroxyl-2-methyl-4-phenyl-1-oxopropyl)-4-(phenylmethyl)-2-oxazolidineselone. Yield: 90.6%. IR (KBr, cm$^{-1}$) 3600, 2978.8, 1718.4, 1494.3, 1158.2, 948.2, 703.1, 542.1, 409.0; $^1$H NMR δ 7.40 (m, 10H), 5.58 (dq, 1H, J=6.9 Hz, J=4.5 Hz), 5.35 (m, 1H), 5.00 (m, 1H), 4.33 (m, 1H), 3.11 (dd, 1H, J=13.4 Hz, J=3.6 Hz), 2.95 (d, 1H, 13.1 Hz), 2.57 (dd, 1H, J=13.4 Hz, J=10.1 Hz), 1.27 (d, 3H, 6.9 Hz); $^{13}$C NMR δ 188.62, 177.63, 141.18, 134.94, 129.28, 129.03, 128.37, 127.73, 127.50, 126.41, 73.79, 72.07, 60.57, 44.35, 37.43, 11.63. $^{77}$Se δ 449.31 (d, J=5.8 Hz). Anal. Calcd for $C_{20}H_{22}NO_3Se$: (formula weight=402.36), C, 59.70; H, 5.26; N, 3.48. Found: C, 59.65; H, 5.30; N, 3.45. HRMS (FAB) m/z 404.0772 (404.0766 calcd for $C_{20}H_{22}NO_3Se$, M+H).

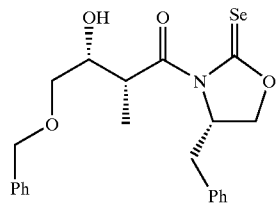

(4S)-3-[3-hydroxyl-2-methyl-4-(phenylmethoxyl]-1-oxopropyl)-4-(phenylmethyl)-2-oxazolidineselone. $^1$H NMR δ 7.25 (m, 10H), 5.26 (dq, 1H, J=6.9 Hz, J=4.3 Hz), 5.01 (m, 1H), 4.63 (s, 2H), 4.35 (m, 2H), 3.49 (m, 2H), 3.27 (dd, 1H, J=13.3 Hz, J=3.6 Hz), 2.75 (d, 1H, J=3.8 Hz), 2.66 (dd, 1H, J=13.3 Hz, J=10.3 Hz), 1.33 (d, 3H, J=7.0 Hz); $^{13}$CNMR δ 188.60, 176.82, 137.85, 135.04, 129.31, 129.06, 128.46, 127.80, 127.48, 73.35, 72,05, 71.60, 70.81, 60.73, 40.39, 37.59, 11.50; $^{77}$Se NMR δ 447.14 (d, J=5.5 Hz). HRMS(FAB) m/z 492.1287 (492.1291 calcd for $C_{24}H_{30}NO_5Se$, M+H)

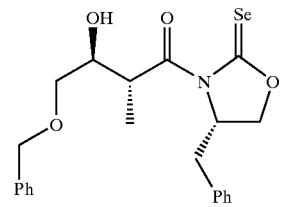

(4S)-3-[3-hydroxyl-2-methyl-4-(phenylmethoxyl]-1-oxopropyl)4(phenylmethyl)-2oxazolidineselone. Yield: 99.4%. IR (KBr, cm$^{-1}$) 3500, 3027.8, 2920.5, 2863.3, 1697.5, 1500, 1450, 1354.2, 1300, 1280, 1200, 1150, 1100, 946.5, 750, 696.5; $^1$H NMR δ 7.40(m, 10H), 5.45 (p, 1H, J=6.9 Hz), 4.97 (m, 1H), 4.63 (ABq, 2H, J=12.0 Hz), 4.32 (m, 2H), 4.11 (m, 1H), 3.73 (m, 2H), 3.41 (d, 1H, J=8.5 Hz), 3.29 (dd, 1H, J=13.5 Hz, J=3.4 Hz), 2.63 (dd, 1H, 13.5 Hz, J=10.2 Hz), 1.29 (d, 3H, J=6.7 Hz); $^{13}$C NMR δ 189.06, 177.58, 137.90, 135.21, 129.39, 129.00, 128.42, 127.81, 127.77, 127.38, 74.35, 73.51, 72.05, 71.99, 60.98, 40.36, 37.27, 14.89; $^{77}$Se NMR δ 441.46 (bd, J=5.5 Hz). HRMS (FAB) m/z 492.1287 (492.1291 calcd for $C_{24}H_{30}NO_5Se$, M+H)

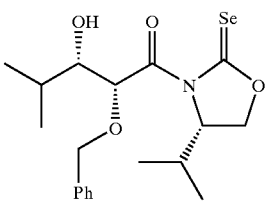

(4S)-4-(1-methylethyl)-3-[(phenylmethoxy)acetyl]-2-oxazolidineselone. $^1$H NMR δ 7.45 (m, 5H), 5.28 (s, 2H), 4.80 (td, 1H, J=8.1 Hz, J=3.6 Hz), 4.73 (s, 2H), 4.49 (m, 2H), 2.43 (dh, 1H, J=7.0 Hz, J=3.6 Hz), 0.99 (d, 3H, J=7.0 Hz), 0.93 (d, 3H, J=7.0 Hz); $^{13}$C NMR δ 188.54, 170.96, 128.51, 128.19, 128.07, 73.58, 72.28, 70.32, 64.30, 28.78, 18.13, 14.94; $^{77}$Se NMR δ 448.9 (br s).

(4S)-4-(1-methylethyl)-3-[3-hydroxyl-4-methyl-2-(phenylmethoxy)-1-oxopentyl]-2-oxazolidineselone. Yield: 63%. $^1$H NMR δ 7.45 (m, 5H), 6.68 (d, 1H, J=2.0 Hz), 4.94 (dt, 1H, J=6.7 Hz, J=3.5 Hz), 4.76 (d, 1H, J=11.1 Hz), 4.49 (ABq, 2H, J=9.0 Hz), 3.91 (m, 1H), 2.35 (dh, 1H, J=7.0 Hz, J=3.5 Hz), 2.03 (m, 1H), 1.95 (d, 11.1 Hz), 1.09 (d, 3H, J=7.0 Hz), 1.06 (d, 3H, J=7.0 Hz), 0.94 (d, 3H, J=7.0 Hz), 0.87 (d, 3H, J=6.9 Hz); $^{13}$C NMR δ 188.64, 172.84, 137.02, 128.62, 128.44, 128.19, 78.93, 72.90, 69.88, 64.01, 32.52, 28.25, 19.25, 19.17, 18.23, 14.66; $^{77}$Se NMR δ 442.5 (d, J=4.8 Hz).

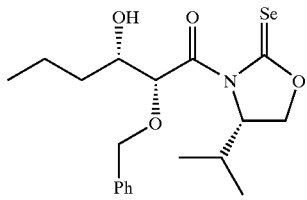

(4S)-4-(1-methylethyl)-3-[3-hydroxyl-2-(phenylmethoxy)-1-oxohexyl]-2-oxazolidineselone. Yield: 90.0%. IR (KBr, cm$^{-1}$) 3500, 2957.8, 2866.8, 1718.4, 1466.3, 1368.3, 1319.3, 1277.3, 1200.3, 1151.2, 1011.2, 950, 905, 829.1, 750, 696.1; $^1$H NMR δ 7.40 (m, 4H), 6.49 (d, J=2.2 Hz), 4.86 (p, 1H, J=4.1 Hz), 4.86 (Abq, 2H, J=11.4 Hz), 4.45 (m, 2H), 4.29 (m, 1H), 2.35 (dhep, 1H, J=7.0 Hz, J=3.7 Hz), 2.12 (d, 1H, J=10.2 Hz), 1.70 (m, 2H), 1.60 (m, 1H), 1.40 (m, 1H), 0.98 (t, 3H, J=7.3 Hz), 0.96 (d, 3H, J=7.2 Hz), 0.92 (d, 3H, J=6.9 Hz); $^{13}$C NMR δ 188.84, 172.17, 137.04, 128.64, 128.41, 128.18, 79.44, 73.13, 72.63, 70.00, 63.94, 35.94, 28.61, 18.94, 18.12, 14.85, 13.98; $^{77}$Se NMR δ 428.5 (d, J=4.7 Hz). Anal. Calcd for $C_{19}H_{27}NO_4Se$ (formula weight=412.43), C, 55.32; H, 6.61; N, 3.40. Found: C, 55.03; H, 6.30; N, 3.70. HRMS (FAB) m/z 414.1172 (414.1185 calcd for $C_{19}H_{28}NO_4Se$, M+H)

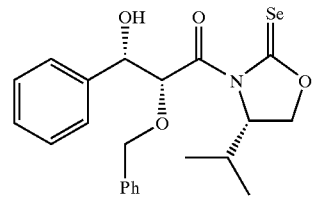

(4S)-4-(1-methylethyl)-3-[3-hydroxyl-3-phenyl-2-(phenylmethoxy)-1oxopropyl]-2-oxazolidineselone. Yield: 97.0%. IR (KBr, cm$^{-1}$) 3464.5, 2927, 1696, 1603.9, 1454.3, 1342.9, 1264.3, 1030, 809, 759, 729, 698, 554, 510; $^1$H NMR δ 7.40 (m, 10H), 6.88 (d, 1H, 3.18 Hz), 5.45 (dd, 1H, J=8.1 Hz, J=3.2 Hz), 4.80 (td, 1H, J=8.8 Hz, J=3.8 Hz), 4.62 (d, 1H, J=11.8 Hz), 4.51 (d, 1H, J=11.8 Hz), 4.38 (m, 2H), 3.00 (d, 1H, J=8.1 Hz), 2.26 (dh, 1H, J=7.0 Hz, J=3.6 Hz), 0.94 (d, 3H, J=7.0 Hz), 0.80 (d, 3H, J=6.9 Hz); $^{13}$C NMR δ 188.79, 171.76, 139.38, 136.73, 128.45, 128.24, 128.13, 128.03, 127.85, 79.80, 74.28, 73.36, 69.78, 63.97, 28.38, 18.16, 14.63; $^{77}$Se NMR δ 442.84 (d, J=4.3 Hz). HRMS (FAB) m/z 448.1020 (448.1028 calcd for $C_{22}H_{26}NO_5Se$, M+H)

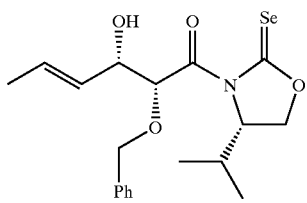

(4S)-4-(1-methylethyl)-3-[3-hydroxyl-2-(phenylmethoxy)-1-oxo-4-hexen-1-yl]-2-oxazolidineselone, Yield: 85.0%. IR (KBr, cm$^{-1}$) 3600, 3027.8, 2964.8, 2859.7, 1725.4, 1480.3, 1398.3, 1277.3, 1200.3, 1144.2, 1018.2, 829.1, 752.1, 703.1, 584.1; $^1$H NMR δ 7.40 (m, 4H), 6.63 (d, 1H, J=3.6 Hz), 5.80 (m, 2H), 4.71 (m, 4H), 4.40 (m, 2H), 2.58 (d, 1H, J=7.8 Hz), 2.27 (dhep, 1H, J=7.0 Hz, J=3.7 Hz), 1.75 (d, 3H, J=6.0 Hz), 0.94 (d, 3H, J=7.0 Hz), 0.88 (d, 3H, J=6.9 Hz); $^{13}$C NMR δ 188.92, 171.67, 136.98, 129.30, 128.72, 128.31, 128.16, 78.93, 73.88, 73.49, 69.81, 63.93, 28.65, 18.05, 17.82, 14.81; $^{77}$Se NMR δ 441.94 (d, J=4.9 Hz). HRMS (FAB) m/z 412.1039 (412.1028 calcd for $C_{19}H_{26}NO_4Se$, M+H).

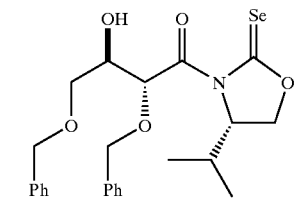

(4S)-4-(1-methylethyl)-3-[3-hydroxyl-2,4-di(phenylmethoxy)-1-oxobutyl]-2-oxazolidineselone. Yield: 99.4%. IR(KBr, cm$^{-1}$) 3480.6, 2869.67, 1700.99, 1496.48, 1475.2, 1384.05, 1368.3, 1356.11, 1310.46, 1282.8, 1269.99, 1204.32, 1160.37, 1133, 1110, 1085.89, 1053.88, 1042.2, 965.14, 943.16, 830, 759, 739, 703, 571; $^1$H NMR δ 7.33 (m, 10H), 6.78 (d, 1H, J=8.3 Hz) (for the $J_{H-Se}$ there was observed a dd, J=8.27, J=5.0 Hz), 4.65 (m, 3H), 4.42 (m, 3H), 4.10 (m, 2H), 3.89 (dd, 1H, J=10.0 Hz, J=3.7 Hz), 3.77 (dd, 1H, J=10.0 Hz, J=3.1 Hz), 3.40 (d, 1H, J=10.8 Hz), 2.30 (dh, 1H, J=7.0 Hz, J=4.0 Hz) 0.90 (d, 3H, J=7.0 Hz), 0.84 (d, 3H, J=7.0 Hz); $^{13}$C NMR δ 189.77, 173.82, 138.17, 137.04, 129.12, 128.35, 128.29, 128.19, 127.61, 73.54, 73.37, 73.30, 70.18, 69.81, 64.44, 28.82, 17.94, 14.88; $^{77}$Se NMR δ 439.97 (dt, J=5.0 Hz, J=1.5 Hz). HRMS (FAB) m/z 492.1287 (492.1291 calcd for $C_{24}H_{30}NO_5Se$, M+H)

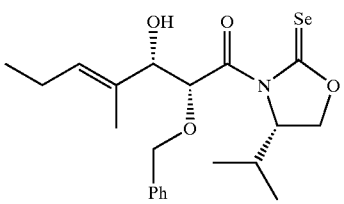

(4S)-4-(1-methylethyl)-3-[3-hydroxyl-4-methyl-2-(phenylmethoxy)-1-oxo-4-hepten-1-yl]-2-oxazolidineselone. Yield: 63%. $^{77}$Se NMR δ 418.7, 427.6 ppm.

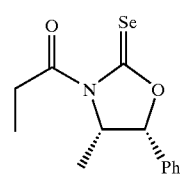

(4R, 4α, 5α)-4-methyl-5-phenyl-3-acetyl-2-oxazolidineselone

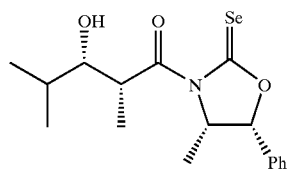

(4R, 4α, 5α)-4-methyl-3-(2,4-dimethyl-3-hydroxyl-1-oxopentyl)-5-phenyl-2-oxazolidineselone. Yield: 80.7%. IR (KBr, cm$^{-1}$), 3600, 2957, 1693.9, 1349.4, 1268.4, 1187.3, 930.6, 761.8, 700.9, 633.4, 471.3; $^1$H NMR δ 7.45 (m, 5H), 5.77 (d, 1H, J=7.4), 5.32 (dq, 1H, J=7.1 Hz, J=2.6 Hz), 5.04 (p, 1H, J=6.7 Hz), 3.72 (td, 1H, J=2.9 Hz, J=8.7 Hz), 2.88 (d, 1H, J=3.3 Hz), 1.80 (m, 1H), 1.31 (d, 3H, J=7.0 Hz), 1.11 (d, 3H, J=6.6 Hz), 1.0 (dd, 3H, J=6.6 Hz, J=1.2 Hz); $^{13}$C NMR δ 188.49, 179.35, 131.90, 129.14, 128.80, 125.98, 84.98, 76.37, 59.81, 40.13, 30.90, 19.44, 18.93, 14.29, 10.49; $^{77}$Se NMR δ 5 451.8. HRMS (FAB) m/z 370.0917 (370.0922 calcd for $C_{17}H_{24}NO_3Se$, M+H)

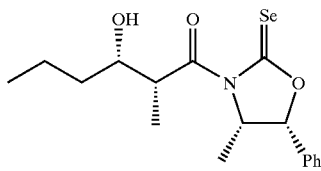

(4R, 4α, 5α)-4-methyl-3-(3-hydroxyl-2-methyl-1-oxohexyl)-5-phenyl-2-oxazolidineselone. Yield: 86.9%. IR(KBr, cm$^{-1}$) 3531.9, 2936.8, 2873.8, 1690.4, 1452.3, 1380, 1370, 1300, 1275, 1200, 1193, 1190, 1150, 1120, 1090, 969.2, 703, 598; $^1$H NMR δ 7.45 (m, 5H), 5.78 (d, 1H, J=7.4 Hz), 5.16 (dq, 1H, J=7.0 Hz, J=2.7 Hz), 5.06 (p, 1H, J=6.7 Hz), 4.16 (m, 1H), 2.75 (d, 1H, 3.2 Hz), 1.50 (m, 4H), 1.3 (d, 3H, J=7.0 Hz), 1.02 (d, 3H, J=7.0 Hz), 1.01 (t, 3H, J=7.0 ); $^{13}$C NMR δ 188.64, 178.49, 131.85, 129.14, 128.80, 125.98, 85.01, 71.24, 59.83, 42.13, 35.83, 19.19, 18.93, 14.33, 14.08, 10.59; $^{77}$Se NMR δ 460.36 (d, J=5.5 Hz). Anal. Calcd for $C_{17}H_{23}NO_3Se \cdot 1/4H_2O$ (forrmula weight=372.84), C, 54.76; H, 6.23; N, 3.76. Found: C, 55.15; H, 5.72; N, 3.64. HRMS (FAB) m/z 370.0917 (370.0922 calcd for $C_{17}H_{24}NO_3Se$, M+H)

REFERENCES

It is noted that all of the cited references are herein incorporated by reference into this disclosure.
1. Evans, D. A.; Bartroli, J.; Shih, T. L. *J. Am. Chem. Soc.* 1981, 103 (8), 2127.
2. Heathcock, C. H. *Mod. Synth. Meth.* 1992, 1.
3. Mahwald, R. *Chem. Rev.* 1999, 99, 1095.
4. Bach, T. *Angew. Chem., Int. Ed. Engl.* 1994, 33, 417. Nelson, S. G. *Tetrahedron Asymmetry* 1998, 9, 357. Also see, Ghosh, A.K.; Mathivanan, P.; Cappiello, J. *Tetrahedron Asymmetry* 1998, 9, 1.
5. Silks, L. A.; Dunlap, R. B.; Odom, J. D. *J. Am. Chem. Soc.* 1990, 112, 4979. Silks, L. A.; Peng, J.; Odom, J. D.; Dunlap, R. B. *J. Chem. Soc., Perkins Trans.* 1 1991, 2495. Silks, L. A.; Peng, J.; Dunlap, R. B.; Odom, J. D. *J. Org. Chem.* 1991, 56, 6733. Peng, J.; Odom, J. D.; Dunlap, R. B.; Silks, L. A. *Tetrahedron Asymmetry* 1994, 5(9), 1627. Peng, J.; Ashburn, D. A.; Barr, M. E.; Lebioda, L.; Martinez, R. A.; Garber, A. R.; Odom, J. D.; Dunlap, R. B.; Silks, L. A. *J. Org. Chem.* 1995, 60 (17), 5540. Wu, R.; Odom, J. D.; Dunlap, R. B.; Silks, L. A. *Tetrahedron Asymmetry* 1995, 6(4), 833. Wu, R.; Silks, L. A.; Odom, J. D.; Dunlap, R. B. *Spectroscopy* 1996, 11 (6), 37. Wu, R.; Hemandez, G.; Odom, J. D.; Dunlap, R. B.; Silks, L. A. *Chem. Commun.* 1996, (10), 1125. Wu, R.; Barr, M. E.; Hernandez, G.; Silks, L. A. *Recent Res. Dev. in Org. Bioorg. Chem.* 1998, 2, 29. Wu, R., Odom, J. D., Dunlap, R. B., Silks, L. A *Tetrahedron Asymmetry* 1999,10(8), 1465.
6. Peng, J.; Barr, M.; Ashburn, D. A.; Odom, J. D.; Dunlap, R. B.; Silks, L. A. *J. Org. Chem.* 1994, 59, 4977.
7. Crimmins, M. T.; King, B. W.; Tabet, E. A. *J. Am. Chem. Soc.* 1997, 119, 7883.
8. Yan, T.-H.; Jung, A.-W.; Lee, H.-C.; Chang, C.-S.; Liu, W.-H. *J. Org. Chem.* 1995, 60, 3301, and references cited therein.
9. $^1$H—$^1$H DQF-COSY NMR solution experiments are being performed to help ascertain the enolate geometry.
10. Assignment of the aldol configuration is based on the well established fact that $J_{threo}$ (7–9 Hz)>$J_{erythro}$ (3–6 Hz). See, Wang, Y.-C.; Su, D.-W.; Lin, C.-M.; Tseng, H.-L.; Li, C.-L.; Yan, T.-H. *J. Org. Chem.* 1999, 64, 6495 and references cited therein.
11. For aldol reactions see Mukaiyama, M. T.; Shiina, H.; Uchiro; Kobayashi, S. *Bull. Chem. Soc. Jpn.* 1994, 67, 1708. Mukaiyama, T. *Aldrichim. Acta* 1996, 29, 59. Kanda, Y.; Fukuyama, T. *J. Am. Chem. Soc.* 1993, 115, 8451. The Takai-Utimoto reaction has been expanded by Boeckman and coworkers to provide high levels of stereocontrol in the synthesis of anti/syn triads. See, Boeckman, R. K.; Hudack, R. A. *J. Org. Chem.* 1998, 63, 3324 and references cited therein. Burke has reacted trans-propenyllithium in the presence of $ZnBr_2$ with a protected D-glyceraldehyde (a Mukaiyama reaction) to give rise to the anti alcohol with 8:1 diastereoselectivity. See, Burke, S. D.; Jian, H.; Mongin, A. P. *Tetrahedron Left.* 1998, 39, 2239.
12. The rotation of the diol, $[α]^{24}_D$=+10° (c=0.006, CHCl$_3$), compares favorably to its reported value ($[α]^{24}_D$=+10.29° (c=0.91, CHCl$_3$)]. Garcia, J.; Kim, B.-M.; Masamune, S. *J. Org. Chem.* 1987, 52, 4831. This value also compares favorably with that reported for its enantiomer ($[α]^{24}_D$=−10.42° (c=0.96, CHCl$_3$)]. Rychnovsky, S. D.; Hoye, R. C. *J. Am Chem. Soc.* 1994, 116, 1753.
13. Su, D.-W.; Wang, Y.-C; Yan, T.-H. *Tetrahedron Left.* 1999, 40, 4197.
14. Houk, K. N.; Menzer, S.; Newton, S. P.; Raymo, F. M.; Stoddart, J. F.; Williams, D. J. *J. Am. Chem. Soc.* 1999, 121, 1479 and references cited therein.
15. Novoa, J. J.; Carme Rovira, M.; Rovira, C.; Veciane, J.; Tarres, J. *Adv. Mater.* 1995, 7, 233. Also see, Desiraju, G. R. *Acc. Chem. Res.* 1996, 29 (9), 441.
16. Iwaoka, M.; Tomoda, S. *J. Am. Chem. Soc.* 1994, 116, 4463.
17. Narayanan, S. J.; Sridevi, B.; Chandrashekar, T. K.; Vij, A.; Roy, R. *Angew. Chem. Int Ed. Engl.* 1998, 37(24), 3394.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. An aldol condensation synthesis method for generating a two chiral center compound that is selectively a syn or anti 1,2-diol containing product isomer, comprising the steps:

a) obtaining a chiral 2-oxazolidineselone as an aldol acceptor;
b) mixing said obtained chiral 2-oxazolidineselone with a first quantity of Lewis acid and reacting for a first reaction period;
c) mixing with said first reaction period mixture an amine and reacting for a second reaction period to generate an enolate solution;
d) mixing with said enolate solution an aldehyde as an aldol donor and reacting for a third reaction period to favor selectively producing the syn isomer product or producing no diastereoselectivity or mixing with said aldol donor that is precomplexed with a second quantity of said Lewis acid and reacting for said third reaction period to favor selectively producing the anti isomer product, wherein said syn or anti isomer product contains a selone auxiliary;
e) quenching with a proton source said third reaction period mixture;
f) removing the selone auxiliary to produce the two chiral center compound that is selectively a syn or anti 1,2-diol containing isomer product; and
g) isolating the syn or anti 1,2-diol containing isomer product.

2. An aldol condensation synthesis method according to claim 1, wherein said obtained chiral 2-oxazolidineselone is an N-acyl chiral 2-oxazolidineselone and said aldol donor is an aldehyde.

3. An aldol condensation synthesis method according to claim 1, wherein said Lewis acid is $TiCl_4$.

4. An aldol condensation synthesis method according to claim 1, wherein said amine is a tertiary amine.

5. An aldol condensation synthesis method according to claim 4, wherein said tertiary amine is dusopropylethylamine.

6. An aldol condensation synthesis method according to claim 1, wherein said first reaction period is conducted at a first temperature range, said second reaction period is conducted at a second temperature range, and said third reaction period is conducted at a third temperature range.

7. An aldol condensation synthesis method according to claim 6, wherein said first and said second temperature ranges are approximately equal to one another.

8. An aldol condensation synthesis method according to claim 6, wherein said third temperature range is lower than said first and said second temperature ranges.

9. An aldol condensation synthesis method according to claim 6, wherein said first and said second temperature ranges are approximately equal and fall from about room temperature to about −50° C.

10. An aldol condensation synthesis method according to claim 6, wherein said first and said second temperature ranges are approximately equal and fall from about 10° C. to about −30° C.

11. An aldol condensation synthesis method according to claim 6, wherein said third temperature range is from about room temperature to about −100° C.

12. An aldol condensation synthesis method according to claim 6, wherein said third temperature range is from about room temperature to about −90° C.

13. An aldol condensation synthesis method for generating a two chiral center compound that is selectively a syn or anti 1,2-diol unit containing isomer from a chiral 2-oxazolidineselone comprising the steps:
a) obtaining an N-acyl chiral 2-oxazolidineselone as an aldol acceptor;
b) mixing said obtained N-acyl chiral 2-oxazolidineselone with a first quantity of Lewis acid and reacting for a first reaction period;
c) mixing with said first reaction period mixture a tertiary amine and reacting for a second reaction period to generate an enolate solution;
d) mixing with said enolate solution an aldehyde as an aldol donor and reacting for a third reaction period to favor selectively producing the syn isomer product or producing no diastereoselectivity or mixing with said aldehyde that is precomplexed with a second quantity of said Lewis acid and reacting for said third reaction period to favor producing the anti isomer product, wherein said syn or anti isomer product contains a selone auxiliary;
e) quenching with a proton source said third reaction period mixture;
f) removing the selone auxiliary to produce the two chiral center compound that is selectively a syn or anti 1,2-diol containing isomer product; and
g) isolating the syn or anti 1,2-diol containing isomer product.

14. An aldol condensation synthesis method according to claim 13, wherein said Lewis acid is $TiCl_4$.

15. An aldol condensation synthesis method according to claim 13, wherein said tertiary amine is diisopropylethylamine.

16. An aldol condensation synthesis method according to claim 13, wherein said first reaction period is conducted at a first temperature range, said second reaction period is conducted at a second temperature range, and said third reaction period is conducted at a third temperature range.

17. An aldol condensation synthesis method according to claim 16, wherein said first and said second temperature ranges are approximately equal to one another.

18. An aldol condensation synthesis method according to claim 16, wherein said third temperature range is lower than said first and said second temperature ranges.

19. An aldol condensation synthesis method according to claim 16, wherein said first and said second temperature ranges are approximately equal and fall from about room temperature to about −50° C.

20. An aldol condensation synthesis method according to claim 16, wherein said first and said second temperature ranges are approximately equal and fall from about room temperature to about −30° C.

21. An aldol condensation synthesis method according to claim 16, wherein said third temperature range is from about room temperature to about −100° C.

22. An aldol condensation synthesis method according to claim 16, wherein said third temperature range is from about room temperature to about −90° C.

23. An aldol condensation synthesis method for generating a two chiral center compound that is selectively a syn or anti 1,2-diol unit containing isomer from a chiral 2-oxazolidineselone comprising the steps:
a) obtaining an N-acyl chiral 2-oxazolidineselone as an aldol acceptor;
b) mixing said obtained N-acyl chiral 2-oxazolidineselone with a first quantity of $TiCl_4$ and reacting for a first reaction period and a first temperature range;
c) mixing with said first reaction period mixture diisopropylethylamine and reacting for a second reaction period and a second temperature range to generate an enolate solution;
d) mixing with said enolate solution an aldehyde as an aldol donor and reacting for a third reaction period and a third temperature range to favor selectively producing the syn isomer product or producing no diastereoselectivity or mixing with said aldehyde that is precomplexed with a second quantity of $TiCl_4$ and reacting for said third reaction period and said third temperature range to favor producing the anti isomer product, wherein said syn or anti isomer product contains a selone auxiliary;

e) quenching with a proton source said third reaction period mixture at said third temperature range;

f) removing the selone auxiliary to produce the two chiral center compound that is selectively a syn or anti 1,2-diol containing isomer product; and g) isolating the syn or anti 1,2-diol containing isomer product.

24. An aldol condensation synthesis method according to claim 23, wherein said first and said second temperature ranges are approximately equal to one another.

25. An aldol condensation synthesis method according to claim 23, wherein said third temperature range is lower than said first and said second temperature ranges.

26. An aldol condensation synthesis method according to claim 23, wherein said first and said second temperature ranges are approximately equal and fall from about room temperature to about −50° C.

27. An aldol condensation synthesis method according to claim 23, wherein said first and said second temperature ranges are approximately equal and fall from about room temperature to about −30° C.

28. An aldol condensation synthesis method according to claim 23, wherein said third temperature range is from about room temperature to about −100° C.

29. An aldol condensation synthesis method according to claim 23, wherein said third temperature range is from about room temperature to about −90° C.

* * * * *